United States Patent [19]

Yu et al.

[11] 4,316,902

[45] Feb. 23, 1982

[54] THERAPEUTIC COMPOSITIONS AND VEHICLES FOR TOPICAL PHARMACEUTICALS

[76] Inventors: Ruey J. Yu, 4 Lindenwold Ave., Ambler, Pa. 19002; Eugene J. Van Scott, 1138 Sewell La., Rydal, Pa. 19046

[21] Appl. No.: 77,726

[22] Filed: Sep. 21, 1979

[51] Int. Cl.$^3$ .................... A61K 31/455; A61K 31/05
[52] U.S. Cl. ....................................... 424/266; 424/60; 424/243; 424/317; 424/318; 424/346; 424/355; 424/365
[58] Field of Search ...................... 424/346, 266, 365

[56] References Cited

U.S. PATENT DOCUMENTS

| | | | |
|---|---|---|---|
| 3,666,863 | 5/1972 | Swanbeck | 424/316 |
| 4,067,975 | 1/1978 | Yu et al. | 424/240 |
| 4,178,373 | 12/1979 | Klein et al. | 424/233 |
| 4,203,969 | 5/1980 | Yarrow et al. | 424/83 |

*Primary Examiner*—Leonard Schenkman
*Attorney, Agent, or Firm*—LeBlanc, Nolan, Shur & Nies

[57] ABSTRACT

Non-sticky anhydrous bases useful as vehicles for cosmetics and therapeutic compositions to be topically applied are disclosed. The anhydrous base is composed of two essential ingredients namely isopropyl myristate or isopropyl palmitate and glyceryl monostearate in a concentration of more than 30% for the former by weight of the total composition. The base is excellent as a vehicle for cosmetics and also for pharmaceuticals to be topically applied in the treatment of skin disorders.

11 Claims, No Drawings

THERAPEUTIC COMPOSITIONS AND VEHICLES FOR TOPICAL PHARMACEUTICALS

This invention relates to an improved vehicle for cosmetics or topically applied medicinal products. This vehicle is a stable nonaqueous base which feels neither sticky nor greasy when topically applied to human skin. The vehicle of this invention then is suitable for application of a cosmetic or a medicinal composition to alleviate skin conditions or skin disorders. For example, an alphahydroxy acid such as glycolic acid may be incorporated into the base for the treatment of dry skin conditions by topical application. Dithranol or a corticosteroid such as hydrocortisone or hydrocortisone-17-valerate may be incorporated into the base for the treatment of inflammatory skin disorders such as psoriasis, eczema and seborrheic dermatitis by topical application.

Although anhydrous petrolatum base is a useful vehicle for a pharmaceutical drug for topical administration, the resulting composition exhibits an undesirable greasy and sticky feeling when topically applied on the skin. The medicinal composition formulated with such anhydrous petrolatum base also spreads with difficulty. Therefore, most patients are extremely reluctant to use this kind of product.

This invention then includes the development of a non-sticky anhydrous base which will be stable when stored for prolonged periods at, for example, 40° C. and stable to freezing and thawing. The anhydrous base of this invention is also chemically and physically compatible with drugs for topical administration.

DESCRIPTION OF THE INVENTION

It has been discovered that a non-sticky anhydrous base may be successfully formulated by utilizing a high concentration of isopropyl myristate or isopropyl palmitate with glyceryl monostearate. Although other cosmetic ingredients such as spermaceti, beeswax, stearic acid, stearyl alcohol or cetyl alcohol may be substituted for glyceryl monostearate the anhydrous base thus formulated appears to exhibit a granular and less homogeneous consistency.

The concentration of isopropyl myristate or isopropyl palmitate ranges from 30-to-90% by weight of the total composition. The preferred concentration, however, ranges from 50-to-80%. The concentration of glyceryl monostearate ranges from 10-to-30% by weight of the total composition. The preferred concentration, however, ranges from 15-to-25%. The anhydrous base thus formulated appears pearly white and exhibits the desired homogeneous consistency. The base of this invention also spreads readily and smoothly on the skin, and feels neither sticky nor greasy.

Since the anhydrous base formulated from glyceryl monostearate and isopropyl myristate or isopropyl palmitate of the present invention is very non-sticky during and after the topical application onto the skin other cosmetic ingredients may be added, if desired, to achieve a particular desired consistency. For example, if the anhydrous base is intended for use in a topical treatment of dry skin or inflammatory skin disorders such as psoriasis and eczema, mineral oil may be added to the base to enhance its occlusiveness. Generally, mineral oil is incorporated in the base of the present invention usually at a concentration of less than 30% by weight of the total composition. If petrolatum is to be incorporated in the base of the present invention it is usually present at a concentration of less than 20% by weight of the total composition.

Numerous cosmetic substances and pharmaceutical compounds may be incorporated in the anhydrous base of the present invention. Cosmetic substances and pharmaceutical compounds in liquid or fine powder form may be directly mixed with a warm melted anhydrous base of this invention or dissolved in organic solvents such as ethanol and acetone and then admixed with the base of this invention.

Typical cosmetic and pharmaceutical substances include the following: alphahydroxy acids and analogues such as lactic acid, glycolic acid, mandelic acid, tartaric acid, saccharic acid and ethyl pyruvate; corticosteroids such as hydrocortisone, hydrocortisone-21-acetate, hydrocortisone-17-valerate, hydrocortisone-17-butyrate and triamcinolone acetonide; dithranol; 6-aminonicotinamide and 6-aminonicotinic acid methyl ester; p-aminobenzoic acid and p-aminobenzoic acid esters; and coal tar products.

In our prior U.S. Patents, for example, U.S. Pat. Nos. 3,879,537 and 3,920,835, and in our copending patent application Ser. No. 870,114, filed Jan. 17, 1978, and in our copending patent application entitled Topical Treatment of Dry Skin, filed July 25, 1979, the topical treatment of skin disorders with alpha hydroxy acids and related compounds was disclosed. Several of these compounds were also disclosed as additives to enhance the activity of corticosteroids against certain skin disorders in our copending patent application entitled Additives Enhancing Topical Corticosteroid Action, filed Aug. 9, 1979.

In our U.S. Pat. Nos. 4,067,975 and 4,141,977, the activity of 6-aminonicotinamide, thionicotinamide and related compounds in treating psoriasis by topical application was disclosed. In our copending patent application Ser. No. 9,589, filed Feb. 5, 1979, the activity of nicotinamide analogues was similarly disclosed.

Also, in our patent application entitled Dithranol Compositions Stabilized with Alpha Hydroxy Acids, filed on even date herewith the use of said acids to stabilize dithranol in an antiinflammatory composition for topical application was disclosed.

The anhydrous base of this invention being capable of use as a vehicle in any of the compositions disclosed in the above patents and patent application, the disclosures thereof are hereby incorporated by reference.

PREPARATION OF THE COMPOSITIONS

To formulate the anhydrous base of the present invention glyceryl monostearate and isopropyl myristate or isopropyl palmitate are heated to about 60° C. until all the glyceryl monostearate has been melted. The melted solution is poured into a preheated mixing bowl and the solution is agitated during the period of cooling. The mixing is continued until the solution is congealed to yield a white pearly cream. Generally the concentration of glyceryl monostearate ranges from 10-to-30% by weight of the total composition. The preferred concentration, however, ranges from 15-to-25%. Pure glyceryl monostearate, flake form, glyceryl monopalmitate or a mixture thereof as a commercial product may be utilized in the formulation of the anhydrous base. A preferred flake form of glyceryl monostearate is obtainable commercially from, for example, Amend Drug and Chemical Company of Irvington, N.J. or Van Dyk and Company of Belleville, N.J.

The concentration of isopropyl myristate or isopropyl palmitate ranges from 30-to-90% by weight of the total composition. The preferred concentration, however, ranges from 50-to-80%.

When mineral oil and petrolatum are to be incorporated into the composition to improve the occlusiveness of the base the concentrations used are preferably less than 30% and 20% respectively by weight of the total composition.

A typical anhydrous base of non-sticky nature is formulated from 25% glyceryl monostearate and 75% isopropyl myristate or isopropyl palmitate. When mineral oil is incorporated into the composition a typical anhydrous base for dermatologic usage may consist of 20% glyceryl monostearate, 10% mineral oil and 70% isopropyl myristate or isopropyl palmitate. When petrolatum is incorporated into the anhydrous base it is usually at a concentration of 20% or less by weight of the total composition.

Other cosmetic ingredients may also be incorporated into the anhydrous base. These cosmetic ingredients include surfactants such as sorbitan sesquioleate or sorbitan monooleate, squalene, beeswax, spermaceti, squalane, glyceryl monooleate, beef fat, chicken oil, olive oil, safflower oil, and cottonseed oil. The total concentration of these cosmetic ingredients is preferably not to exceed 30% by weight of the total composition.

Therapeutic drugs or agents may be added to the anhydrous base either after or before the base is congealed. For example, a typical alphahydroxy acid composition is prepared by melting a mixture of glyceryl monostearate 20 gm, mineral oil 10 gm and isopropyl myristate 70 gm followed by adding alphahydroxy acid 0.5 gm. The melted mixture is agitated while cooling until it is congealed to a pearly white cream.

A typical hydrocortisone, or hydrocortisone-21-acetate composition is formulated as follows. A mixture of glyceryl monostearate 15 gm, mineral oil 25 gm and isopropyl myristate 60 gm is heated until melting is complete and hydrocortisone or hydrocortisone-21-acetate 1 gm is added to the melted base. The mixture is stirred while cooling until the base is congealed.

A typical composition containing hydrocortisone-17-valerate is formulated as follows. A mixture of glyceryl monostearate 15 gm, mineral oil 25 gm and isopropyl palmitate 60 gm is heated to a complete melting and hydrocortisone-17-valerate 0.2 gm is added to the melted base. The mixture is stirred until it is congealed.

A typical composition containing a sunscreen agent is formulated as follows. A mixture of glyceryl monostearate 18 gm and isopropyl myristate or isopropyl palmitate 77 gm is heated to a complete melting, and ethyl p-aminobenzoate 5 gm is added to the melted base with stirring. Stirring is continued until the base is congealed.

A typical composition containing a 6-aminonicotinic acid ester is formulated as follows. A mixture of glyceryl monostearate 20 gm, mineral oil 25 gm and isopropyl myristate or isopropyl palmitate 55 gm is heated to a complete melting, and methyl 6-aminonicotinate 0.2 gm is added to the melted base with stirring. Stirring is continued until the base is congealed.

A stabilized therapeutic composition containing dithranol may be formulated as follows. A mixture of glyceryl monostearate 20 gm, mineral oil 10 gm and isopropyl myristate or isopropyl palmitate 70 gm is heated to about 65° C. until the mixture is completely melted. Dithranol, also known as anthralin, 0.1 gm and tartaric acid 0.5 gm are added to the melt with agitation. Continue agitation during the cooling process until the mixture is congealed to a yellowish cream.

It has been established in extensive tests that anhydrous bases of the present invention meet standard stability requirements. Samples in glass jars with and without cosmetic agents and pharmaceuticals were stored for more than one month at 45° C., and were subjected to freezing and thawing.

Both cosmetic and topical therapeutic agents have been successfully incorporated in anhydrous bases of this invention. The topical therapeutic compositions, as will be subsequently described, were tested on humans having dry skin, psoriasis and eczema, and proven to be therapeutically effective when applied on a regular basis to cause within about two-to-four weeks time a return of the affected area to normal skin condition.

Accordingly, it is an object of this invention to provide non-greasy anhydrous bases useful as vehicles for cosmetics or for medicinal applications.

It is another object of this invention to provide a cosmetic or medicinal composition containing a cosmetic or pharmaceutical agent in a stable anhydrous base which, when topically applied, will aleviate symptoms of dry skin or inflammatory skin diseases.

These and other objectives will become readily apparent with reference to the following description.

The following are illustrative examples of formulations of non-greasy anhydrous bases useful as vehicles for topical application according to this invention. It should be understood that the following examples are illustrative only and not limitative of the invention. Therefore, any of the cosmetic or pharmaceutical agents may be substituted according to the teachings of this invention in the following formulations.

EXAMPLE 1

Glyceryl monostearate 25 gm and isopropyl myristate or isopropyl palmitate 75 gm are heated to about 60° C. until the mixture is completely melted. The melt is then agitated during the cooling process until it is congealed to a pearly white cream. The composition has a pH 4.6.

EXAMPLE 2

Glyceryl monostearate 20 gm, mineral oil 15 gm and isopropyl myristate or isopropyl palmitate 65 gm are heated to about 65° C. until the mixture is completely melted. The melt is then agitated during the cooling process until it is congealed to a pearly white cream. The composition has a pH 4.4.

EXAMPLE 3

Glyceryl monostearate 20 gm, mineral oil 20 gm and isopropyl myristate or isopropyl palmitate 60 gm are heated to about 65° C. until the mixture is completely melted. The melt is then agitated during the cooling process until it is congealed to a pearly white cream. The composition has a pH 4.5.

EXAMPLE 4

Glyceryl monostearate 20 gm, mineral oil 25 gm and isopropyl myristate or isopropyl palmitate 55 gm are heated to about 65° C. until the mixture is completely melted. The melt is then agitated during the cooling process until it is congealed to a pearly white cream. The composition has a pH 5.1.

EXAMPLE 5

Glyceryl monostearate 20 gm, mineral oil 30 gm and isopropyl myristate or isopropyl palmitate 50 gm are heated to about 65° C. until the mixture is completely melted. The melt is then agitated during the cooling process until it is congealed to a pearly white cream. The composition has a pH 4.9.

EXAMPLE 6

Glyceryl monostearate 15 gm, mineral oil 20 gm and isopropyl myristate or isopropyl palmitate 65 gm are heated to about 65° C. until the mixture is completely melted. The melt is then agitated during the cooling process until it is congealed to a pearly white cream. The composition has a pH 4.4.

EXAMPLE 7

Glyceryl monostearate 15 gm, mineral oil 25 gm and isopropyl myristate or isopropyl palmitate 60 gm are heated to about 65° C. until the mixture is completely melted. The melt is then agitated during the cooling process until it is congealed to a pearly white cream. The composition has a pH 4.1.

EXAMPLE 8

Glyceryl monostearate 20 gm, petrolatum 10 gm and isopropyl myristate or isopropyl palmitate 70 gm are heated to about 70° C. until the mixture is completely melted. The melt is then agitated during the cooling process until it is congealed to a pearly white cream. The composition has a pH 4.3.

EXAMPLE 9

Glyceryl monostearate 20 gm, petrolatum 20 gm and isopropyl myristate or isopropyl palmitate 60 gm are heated to about 70° C. until the mixture is completely melted. The melt is then agitated during the cooling process until it is congealed to a pearly white cream. The composition has a pH 5.0.

EXAMPLE 10

Glyceryl monostearate 25 gm, petrolatum 20 gm and isopropyl myristate or isopropyl palmitate 55 gm are heated to about 70° C. until the mixture is completely melted. The melt is then agitated during the cooling process until it is congealed to a pearly white cream. The composition has a pH 4.9.

EXAMPLE 11

Glyceryl monostearate 23 gm, petrolatum 20 gm and isopropyl myristate or isopropyl palmitate 57 gm are heated to about 70° C. until the mixture is completely melted. The melt is then agitated during the cooling process until it is congealed to a pearly white cream. The composition has a pH 4.9.

EXAMPLE 12

Glyceryl monostearate 15 gm, petrolatum 10 gm, mineral oil 10 gm and isopropyl myristate or isopropyl palmitate 65 gm are heated to about 70° C. until the mixture is completely melted. The melt is then agitated during the cooling process until it is congealed to a pearly white cream. The composition has a pH 3.6.

EXAMPLE 13

Glyceryl monostearate 20 gm, petrolatum 5 gm, mineral oil 5 gm, sorbitan sesquioleate 2 gm and isopropyl myristate or isopropyl palmitate 68 gm are heated to about 70° C. until the mixture is melted. The melt is then agitated during the cooling process until it is congealed to a pearly white cream. The composition has a pH 4.6.

EXAMPLE 14

Glyceryl monostearate 12 gm, petrolatum 13 gm, mineral oil 25 gm and isopropyl myristate or isopropyl palmitate 50 gm are heated to about 70° C. until the mixture is completely melted. The melt is then agitated to pearly white cream. The composition has a pH 4.5.

EXAMPLE 15

Glyceryl monostearate 15 gm, beeswax 10 gm and isopropyl myristate or isopropyl palmitate 75 gm are heated to about 70° C. until the mixture is completely melted. The melt is then agitated during the cooling process until it is congealed to a pearly white cream. The composition has a pH 4.2.

EXAMPLE 16

Glyceryl monostearate 17 gm, petrolatum 5 gm, beeswax 5 gm and isopropyl myristate or isopropyl palmitate 73 gm are heated to about 70° C. until the mixture is completely melted. The melt is then agitated during the cooling process until it is congealed to a pearly white cream. The composition has a pH 4.4.

EXAMPLE 17

Glyceryl monostearate 15 gm, beeswax 10 gm, petrolatum 5 gm and isopropyl myristate or isopropyl palmitate 70 gm are heated to about 70° C. until the mixture is completely melted. The melt is then agitated during the cooling process until it is congealed to a pearly white cream. The composition has a pH 4.4.

EXAMPLE 18

Glyceryl monostearate 20 gm, beef fat 10 gm, purified chicken oil 10 gm and isopropyl myristate or isopropyl palmitate 60 gm are heated to about 70° C. until the mixture is completely melted. The melt is then agitated during the cooling process until it is congealed to a pearly white cream. The composition has a pH 4.9.

EXAMPLE 19

Glyceryl monostearate 20 gm, beef fat 5 gm, purified chicken oil 5 gm, mineral oil 10 gm and isopropyl myristate or isopropyl palmitate 60 gm are heated to about 70° C. until the mixture is completely melted. The melt is then agitated during the cooling process until it is congealed to a pearly white cream. The composition has a pH 5.8.

EXAMPLE 20

Glyceryl monostearate 15 gm, petrolatum 5 gm, mineral oil 25 gm and isopropyl myristate or isopropyl palmitate 55 gm are heated to about 70° C. until the mixture is completely melted. The melt is then agitated during the cooling process until it is congealed to a pearly white cream. The composition has a pH 5.5.

EXAMPLE 21

Glyceryl monostearate 20 gm, beef fat 10 gm, purified chicken oil 10 gm, mineral oil 10 gm and isopropyl myristate or isopropyl palmitate 50 gm are heated to about 70° C. until the mixture is completely melted. The melt is then agitated during the cooling process until it is congealed to a pearly white cream. The composition has a pH 4.6.

EXAMPLE 22

Glyceryl monostearate 20 gm, mineral oil 5 gm and isopropyl myristate or isopropyl palmitate 75 gm are heated to about 65° C. until the mixture is completely melted. The melt is then agitated during the cooling process until it is congealed to a pearly white cream. The composition has a pH 4.3.

EXAMPLE 23

Glyceryl monostearate 25 gm, purified chicken oil 10 gm and isopropyl myristate or isopropyl palmitate 65 gm are heated to 65° C. until the mixture is completely melted. The melt is then agitated during the cooling process until it is congealed to a pearly white cream. The composition has a pH 5.6.

EXAMPLE 24

Glyceryl monostearate 20 gm, mineral oil 5 gm, purified chicken oil 5 gm and isopropyl myristate or isopropyl palmitate 70 gm are heated to about 65° C. until the mixture is completely melted. The melt is then agitated during the cooling process until it is congealed to a pearly white cream. The composition has a pH 5.1.

EXAMPLE 25

Glyceryl monostearate 23 gm, petrolatum 5 gm, sorbitan sesquioleate 2 gm and isopropyl myristate or isopropyl palmitate 70 gm are heated to about 70° C. until the mixture is completely melted. The melt is then agitated during the cooling process until it is congealed to a pearly white cream. The composition has a pH 5.1.

EXAMPLE 26

Glyceryl monostearate 20 gm, purified chicken oil 20 gm and isopropyl myristate or isopropyl palmitate 60 gm are heated to 65° C. until the mixture is completely melted. The melt is then agitated during the cooling process until it is congealed to a pearly white cream. The composition has a pH 3.5.

EXAMPLE 27

Glyceryl monostearate 20 gm, squalene 20 gm and isopropyl myristate or isopropyl palmitate 60 gm are heated to 65° C. until the mixture is completely melted. The melt is then agitated during the cooling process until it is congealed to a pearly white cream. The composition has a pH 4.4.

EXAMPLE 28

Glyceryl monostearate 15 gm, squalene 25 gm and isopropyl myristate or isopropyl palmitate 60 gm are heated to 65° C. until the mixture is completely melted. The melt is then agitated during the cooling process until it is congealed to a pearly white cream. The composition has a pH 4.3.

EXAMPLE 29

Glyceryl monostearate 20 gm, glyceryl monooleate 5 gm and isopropyl myristate or isopropyl palmitate 75 gm are heated to 65° C. until the mixture is completely melted. The melt is then agitated during the cooling process until it is congealed to a pearly white cream. The composition has a pH 4.8.

EXAMPLE 30

Glyceryl monostearate 20 gm, glyceryl monooleate 10 gm and isopropyl myristate or isopropyl palmitate 70 gm are heated to 65° C. until the mixture is completely melted. The melt is then agitated during the cooling process until it is congealed to a pearly white cream. The composition has a pH 5.1.

EXAMPLE 31

Glyceryl monostearate 20 gm, squalane 10 gm and isopropyl myristate or isopropyl palmitate 70 gm are heated to 65° C. until the mixture is completely melted. The melt is then agitated during the cooling process until it is congealed to a pearly white cream. The composition has a pH 4.6.

EXAMPLE 32

Glyceryl monostearate 20 gm, squalane 20 gm and isopropyl myristate or isopropyl palmitate 60 gm are heated to 65° C. until the mixture is completely melted. The melt is then agitated during the cooling process until it is congealed to a pearly white cream. The composition has a pH 4.1.

EXAMPLE 33

Glyceryl monostearate 20 gm, purified chicken oil 15 gm and isopropyl myristate or isopropyl palmitate 65 gm are heated to 65° C. until the mixture is completely melted. The melt is then agitated during the cooling process until it is congealed to a pearly white cream. The composition has a pH 5.8.

EXAMPLE 34

A therapeutic composition of pH 2.2 containing 0.5% tartaric acid in an anhydrous base may be prepared as follows:

Glyceryl monostearate 20 gm, mineral oil 10 gm and isopropyl myristate or isopropyl palmitate 70 gm are heated to 65° C. until the mixture is completely melted. Tartaric acid 0.5 gm is added to the melt with agitation. Continue agitation during the cooling process until the mixture is congealed to a pearly white cream.

EXAMPLE 35

A therapeutic composition of pH 2.3 containing 0.5% tartronic acid in an anhydrous base may be prepared as follows:

Glyceryl monostearate 20 gm, mineral oil 10 gm and isopropyl myristate or isopropyl palmitate 70 gm are heated to 65° C. until the mixture is completely melted. Tartronic acid 0.5 gm is added to the melt with agitation. Continue agitation during the cooling process until the mixture is congealed to a pearly white cream.

EXAMPLE 36

A therapeutic composition of pH 4.0 containing 0.1% dithranol stabilized with 0.5% tartaric acid in an anhydrous base may be prepared as follows:

Glyceryl monostearate 15 gm, petrolatum 10 gm, mineral oil 25 gm and isopropyl myristate or isopropyl palmitate 50 gm are heated to about 70° C. until the mixture is completely melted. Dithranol 0.1 gm and tartaric acid 0.5 gm are added to the melt with agitation. Continue agitation during the cooling process until the mixture is congealed to a yellowish cream.

EXAMPLE 37

A therapeutic composition of pH 2.4 containing 0.05% dithranol stabilized with 0.2% tartronic acid in an anhydrous base may be prepared as follows:

Glyceryl monostearate 20 gm, mineral oil 10 gm and isopropyl myristate or isopropyl palmitate 70 gm are heated to about 65° C. until the mixture is completely melted. Dithranol 0.05 gm and tartronic acid 0.2 gm are added to the melt with agitation. Continue agitation during the cooling process until the mixture is congealed to a yellowish cream.

EXAMPLE 38

A therapeutic composition of pH 3.9 containing 0.1% dithranol stabilized with 0.5% tartaric acid in an anhydrous base may be prepared as follows:

Glyceryl monostearate 15 gm, mineral oil 25 gm and isopropyl myristate or isopropyl palmitate 60 gm are heated to about 65° C. until the mixture is completely melted. Dithranol 0.1 gm and tartaric acid 0.5 gm are added to the melt with agitation. Continue agitation during the cooling process until the mixture is congealed to a bright yellowish cream.

EXAMPLE 39

A therapeutic composition of pH 2.6 containing a 0.02% dithranol stabilized with 0.2% citric acid in an anhydrous base may be prepared as follows:

Glyceryl monostearate 15 gm, mineral oil 20 gm and isopropyl myristate or isopropyl palmitate 65 gm are heated to about 65° C. until the mixture is completely melted. Dithranol 0.02 gm and citric acid 0.2 gm are added to the melt with agitation. Continue agitation during the cooling process until the mixture is congealed to a light yellowish cream.

EXAMPLE 40

A therapeutic composition of pH 3.7 containing 0.1% dithranol stabilized with 0.2% citric acid in an anhydrous base may be prepared as follows:

Glyceryl monostearate 20 gm and isopropyl myristate or isopropyl palmitate 80 gm are heated to about 65° C. until the mixture is completely melted. Dithranol 0.1 gm and citric acid 0.2 gm are added to the melt with agitation. Continue agitation during the cooling process until the mixture is congealed to a yellowish cream.

EXAMPLE 41

A therapeutic composition of pH 3.9 containing 0.03% dithranol stabilized with 0.5% tartaric acid in an anhydrous base may be prepared as follows:

Glyceryl monostearate 20 gm, mineral oil 25 gm and isopropyl myristate or isopropyl palmitate 55 gm are heated to about 65° C. until the mixture is completely melted. Dithranol 0.03 gm and tartaric acid 0.5 gm are added to the melt with agitation. Continue agitation during the cooling process until the mixture is congealed to a light yellowish cream.

EXAMPLE 42

A therapeutic composition of pH 4.8 containing 0.05% dithranol stabilized with 0.2% tartaric acid in an anhydrous base may be prepared as follows:

Glyceryl monostearate 15 gm, mineral oil 25 gm and isopropyl myristate or isopropyl palmitate 60 gm are heated to about 65° C. until the mixture is completely melted. Dithranol 0.05 gm and tartaric acid 0.2 gm are added to the melt with agitation. Continue agitation during the cooling process until the mixture is congealed to a yellowish cream.

EXAMPLE 43

A therapeutic composition of pH 2.6 containing 0.1% dithranol stabilized with 0.5% citric acid in an anhydrous base may be prepared as follows:

Glyceryl monostearate 20 gm, mineral oil 10 gm and isopropyl myristate or isopropyl palmitate 70 gm are heated to about 65° C. until the mixture is completely melted. Dithranol 0.1 gm and citric acid 0.5 gm are added to the melt with agitation. Continue agitation during the cooling process until the mixture is congealed to a yellowish cream.

EXAMPLE 44

A therapeutic composition of pH 2.3 containing 0.05% dithranol stabilized with 0.5% tartaric acid in an anhydrous base may be prepared as follows:

Glyceryl monostearate 20 gm, mineral oil 10 gm and isopropyl myristate or isopropyl palmitate 70 gm are heated to about 65° C. until the mixture is completely melted. Dithranol 0.05 gm and tartaric acid 0.5 gm are added to the melt with agitation. Continue agitation during the cooling process until the mixture is congealed to a yellowish cream.

EXAMPLE 45

A therapeutic composition of pH 2.2 containing 0.05% dithranol stabilized with 0.5% tartronic acid in an anhydrous base may be prepared as follows:

Glyceryl monostearate 20 gm, mineral oil 10 gm and isopropyl myristate or isopropyl palmitate 70 gm are heated to about 65° C. until the mixture is completely melted. Dithranol 0.05 gm and tartronic acid 0.5 gm are added to the melt with agitation. Continue agitation during the cooling process until the mixture is congealed to a yellowish cream.

EXAMPLE 46

A therapeutic composition of pH 3.2 containing 0.05% dithranol, 0.4% tartaric acid and 1% alpha-O-acetyl mandelic acid may be prepared as follows:

Glyceryl monostearate 20 gm, mineral oil 10 gm and isopropyl myristate or isopropyl palmitate 70 gm are heated to 65° C. until the mixture is completely melted. Dithranol 0.05 gm tartaric acid 0.4 gm and alpha-O-acetyl mandelic acid 1 gm are added to the melt with agitation. Continue agitation during the cooling process until the mixture is congealed to a yellowish cream.

EXAMPLE 47

A therapeutic composition of pH 3.2 containing 1% hydrocortisone in an anhydrous base may be prepared as follows:

Glyceryl monostearate 15 gm, mineral oil 25 gm and isopropyl myristate or isopropyl palmitate 60 gm are heated to 65° C. until the mixture is completely melted. Hydrocortisone powder 1 gm is added to the melt with agitation. Continue agitation during the cooling process until the mixture is congealed to a white cream.

EXAMPLE 48

A therapeutic composition of pH 2.6 containing 1% hydrocortisone and 0.5% cysteic acid in an anhydrous base may be prepared as follows:

Glyceryl monostearate 15 gm, mineral oil 25 gm and isopropyl myristate or isopropyl palmitate 60 gm are heated to 65° C. until the mixture is completely melted. Hydrocortisone powder 1 gm and cysteic acid 0.5 gm are added to the melt with agitation. Continue agitation during the cooling process until the mixture is congealed to a white cream.

EXAMPLE 49

A therapeutic composition of pH 3.7 containing 1% hydrocortisone-21-acetate in an anhydrous base may be prepared as follows:

Glyceryl monostearate 17 gm, petrolatum 10 gm, mineral oil 10 gm isopropyl myristate or isopropyl palmitate 63 gm are heated to 70° C. until the mixture is completely melted. Hydrocortisone-21-acetate powder 1 gm is added to the melt with agitation. Continue agitation during the cooling process until the mixture is congealed to a white cream.

EXAMPLE 50

A therapeutic composition of pH 3.9 containing both 1% hydrocortisone-21-acetate and 0.2% ethyl pyruvate in an anhydrous base may be prepared as follows:

Glyceryl monostearate 17 gm, petrolatum 10 gm, mineral oil 10 gm and isopropyl myristate or isopropyl palmitate 63 gm are heated to 70° C. until the mixture is completely melted. Hydrocortisone-21-acetate powder 1 gm and ethyl pyruvate 0.2 ml are added to the melt with agitation. Continue agitation during the cooling process until the mixture is congealed to a white cream.

EXAMPLE 51

A therapeutic composition of pH 5.9 containing 0.2% hydrocortisone-17-valerate in an anhydrous base may be prepared as follows:

Glyceryl monostearate 15 gm, mineral oil 25 gm and isopropyl myristate or isopropyl palmitate 60 gm are heated to 65° C. until the mixture is completely melted. Hydrocortisone-17-valerate powder 0.2 gm is added to the melt with agitation. Continue agitation during the cooling process until the mixture is congealed to a white cream.

EXAMPLE 52

A therapeutic composition of pH 3.4 containing 0.1% 6-aminonicotinamide in an anhydrous base may be prepared as follows:

Glyceryl monostearate 15 gm, petrolatum 10 gm, mineral oil 15 gm and isopropyl myristate or isopropyl palmitate 60 gm are heated to 70° C. until the mixture is completely melted. 6-aminonicotinamide powder 0.1 gm is added to the melt with agitation. Continue agitation during the cooling process until the mixture is congealed to a white cream.

EXAMPLE 53

A therapeutic composition of pH 4.5 containing 0.2% 6-aminonicotinic acid methyl ester in an anhydrous base may be prepared as follows:

Glyceryl monostearate 20 gm, mineral oil 25 gm and isopropyl myristate or isopropyl palmitate 55 gm are heated to 65° C. until the mixture is completely melted. 6-aminonicotinic acid methyl ester 0.2 gm is added to the melt with agitation. Continue agitation during the cooling process until the mixture is congealed to a white cream.

EXAMPLE 54

A therapeutic composition of pH 4.4 containing 2% coal tar and 0.4% tartaric acid in an anhydrous base may be prepared as follows:

Glyceryl monostearate 15 gm, mineral oil 20 gm and isopropyl myristate or isopropyl palmitate 65 gm are heated to 65° C. until the mixture is completely melted. Coal tar solution U.S.P. 10 ml and tartaric acid 0.4 gm are added to the melt with agitation. Continue agitation until the mixture is congealed to a light yellowish cream.

EXAMPLE 55

A therapeutic composition of pH 4.9 containing 0.1% triamcinolone acetonide in an anhydrous base may be prepared as follows:

Glyceryl monostearate 15 gm, mineral oil 15 gm and isopropyl myristate or isopropyl palmitate 70 gm are heated to 65° C. until the mixture is completely melted. Triamcinolone acetonide 0.1 gm and tartaric acid 0.4 gm are added to the melt with agitation. Continue agitation until the mixture is congealed to a white cream.

EXAMPLE 56

A cosmetic composition of pH 3.7 containing 5% ethyl p-aminobenzoate in an anhydrous base may be prepared as follows:

Glyceryl monostearate 18 gm and isopropyl myristate or isopropyl palmitate 77 gm are heated to 60° C. until the mixture is completely melted. Ethyl p-aminobenzoate 5 gm is added to the melt with agitation. Continue agitation until the mixture is congealed to a white cream.

EXAMPLE 57

Glyceryl monostearate 20 gm, olive oil 10 gm and isopropyl myristate or isopropyl palmitate 70 gm are heated to 65° C. until the mixture is completely melted. The melt is then agitated during the cooling process until it is congealed to a white cream. The composition has a pH 4.6.

EXAMPLE 58

Glyceryl monostearate 20 gm, safflower oil 10 gm and isopropyl myristate or isopropyl palmitate 70 gm are heated to 65° C. until the mixture is completely melted. The melt is then agitated during the cooling process until it is congealed to a white cream. The composition has a pH 4.8.

TEST RESULTS

The anhydrous bases of this invention with or without cosmetic or therapeutic agents, were tested for physical stability or instability by examining for transparent oil or liquid formation at 40° C.

Each of the compositions formulated according to the above examples were tested for storage stability in two-ounce jars. The jars were kept at a temperature of 40° C. for an extended period of time of at least one month. In each case, the anhydrous bases of this invention with or without cosmetic or therapeutic agents were stable for a period of at least one month when evaluated according to the above criteria.

In some instances, the cream may start to melt at 40° C. or higher temperature, especially when the content of the glyceryl monostearate is below 20 percent by weight of the total composition. The partially melted liquid, however, will recongeal to the original cream after the mixture is cooled slightly. We have also found that the presence of an alphahyroxy acid in the formulation appears to prevent such partial melting of the cream at 40° C. or higher temperature.

The anhydrous bases of this invention were also evaluated by a freeze-thaw test. In this test each of the anhydrous bases as formulated in the foregoing examples, were subjected to freezing at a temperature of −20° C. for 24 hours and subsequent thawing to room temperature for another 24 hours. In each instance, the anhydrous bases of this invention were found to be stable as determined by the above criteria.

CLINICAL TESTS

Clinical tests were conducted to ascertain whether the anhydrous bases of this invention were nonirritating and nonallergenic to human skin and also to determine whether said anhydrous bases containing pharmaceutical agents were efficacious for topical treatment of various skin disorders including disturbed keratinization and inflammatory dermatoses.

Twenty-one patients having psoriasis and six patients having eczema participated in one study. Evaluations of clinical efficacy of topical pharmaceutical agents on psoriasis are based on the following criteria:

The involved skin in psoriasis is hyperplastic (thickened), erythematous (red or inflamed), and has thick adherent scales. The degree of thickening is such that lesions are elevated up to 1 mm above the surface of adjacent normal skin; erythema is usually an intense red; the thickened adherent scales cause the surface of involved skin to be markedly rough and uneven. These three attributes of thickness, color and texture can be quantified to allow objective measurement of degree of improvement from topically applied therapeutic test materials as follows:

|  | Degree of Improvement | | | | |
| --- | --- | --- | --- | --- | --- |
|  | None (0) | Mid (1+) | Moderate (2+) | Substantial (3+) | Complete (4+) |
| Thickness | Highly elevated | Detectable reduction | Readily apparent reduction | Barely elevated | Normal thickness |
| Texture | Visibly rough | Palpably rough | Uneven but not rough | Slightly uneven | Visibly and palpably smooth |
| Color | Intense red | Red | Dark pink | Light pink | Normal skin color |

Using such parameters degrees of change in lesion can be numerically noted and comparisons made of one treated site to another.

Similar but not identical parameters were also applied to eczema for evaluating efficaciousness of topical agents.

Therapeutic compositions of hydrocortisone, hydrocortisone-21-acetate, hydrocortisone-17-valerate, triamcinolone acetonide, 6-aminonicotinamide, 6-aminonicotinic acid methyl ester and dithranol were prepared according to the Examples. Treatment areas in patients having psoriasis or eczema were localized areas of lesions 4 cm in diameter demarcated with a plastic ring of that size linked on a stamp pad. The medicinal creams were topically applied by the patient in an amount (usually about 0.1 cubic centimeter) sufficient to cover the test site. Applications were made usually three times daily without occlusive dressings. Clinical evaluations of degrees of improvement were made at daily intervals for drugs such as corticosteroids and 6-aminonicotinamide, and at weekly intervals for drugs such as dithranol. Treatment periods generally lasted for two to six weeks, unless clearing of disease occurred earlier, and an evaluation of degree imrpovement was made at that time. The following are the results of these tests.

HYDROCORTISONE

It was discovered that hydrocortisone 1% in anhydrous bases of the present invention was markedly effective in the treatment of the six patients with eczema. Complete resolution of the test sites treated with these medicinal compositions was obtained within a one-to-two week period of time.

In eighteen of twenty-one psoriatic patients tested with hydrocortisone 1% in anhydrous bases of the present invention a substantial to complete clearing of the test sites was achieved within one-to-two weeks.

HYDROCORTISONE-21-ACETATE

Hydrocortisone-21-acetate 1% in anhydrous bases of the present invention was found to be very effective in the treatment of the six patients with eczema. Complete resolution of the test sites treated with these medicinal compositions was obtained within a two week period.

HYDROCORTISONE-17-VALERATE

Hydrocortisone-17-valerate 0.2% in anhydrous bases of the present invention was found to be markedly effective in the treatment of the six patients with eczema. Complete resolution of the test sites treated with these medicinal compositions was obtained within a one-to-two week period of time.

In twenty of twenty-one psoriatic patients tested with hydrocortisone-17-valerate 0.2% in anhydrous bases of the present invention a substantial to complete clearing of the test sites was achieved within one-to-two weeks.

TRIAMCINOLONE ACETONIDE

It was found that triamcinolone acetonide 0.1% in anhydrous bases of the present invention was markedly effective in the treatment of the six patients with eczema. Complete resolution of the test sites treated with these medicinal compositions was obtained within one-to-two weeks.

In twelve psoriatic patients tested with triamcinolone acetonide 0.1% in anhydrous bases of the presnet invention a substantial to complete clearing of the test sites was achieved within one to two weeks.

6-AMINONICOTINAMIDE

It was found that 6-aminonicotinamide 0.1% in anhydrous bases of the present invention was very effective in the treatment of eight patients with psoriasis. Complete resolution of the test sites treated with these medicinal compositions was obtained within one-to-two week periods.

6-AMINONICOTINIC ACID METHYL ESTER 6-aminonicotinic acid methyl ester 0.2% in anhydrous bases of the present invention was found to be markedly efficacious in the treatment of the eight patients with psoriasis. Complete resolution of the test sites treated with these medicinal compositions was obtained within two week periods of time.

DITHRANOL

In eighteen of twenty-one psoriatic patients treated with dithranol 0.1% in anhydrous bases of the present invention substantial to complete clearing of the test sites was achieved within four to six weeks.

ALPHAHYDROXY ACIDS (A) Severe Dry Skin

Four patients having severe dry skin participated in this study. Evaluations of clinical efficacy of topical alphahydroxy acids on patients with severe dry skin are based on the following criteria.

The involved skin on severe dry skin is hyperplastic (thickened) and has thick adherent scales. The degree of thickening is such that lesions are palpably and visibly elevated. The thickened adherent scales cause the surface of involved skin to be markedly rough and uneven. These two attributes of thickness and texture can be quantified to allow objective measurement of degree of improvement from topically applied therapeutic test materials as follows:

|  | Degree of Improvement | | | | |
| --- | --- | --- | --- | --- | --- |
|  | None (0) | Mid (1+) | Moderate (2+) | Substantial (3+) | Complete (4+) |
| Thickness | Highly elevated | Detectable reduction | Readily apparent reduction | Barely elevated | Normal thickness |
| Texture | Visibly rough | Palpably rough | Uneven but not rough | Slightly uneven | Visibly and palpably smooth |

By means of such parameters degrees of change in lesions can be numerically noted and comparisons made of one treated site to another.

In order to evaluate the alphahydroxy acids in anhydrous bases of the present invention a total of four patients with severe dry skin conditions or ichthyosis were treated with the compositions as described in the Examples.

Treated areas were of a size convenient for topical applications, i.e., circles 4 cm in diameter demarcated with a plastic ring of that size inked on a stamp pad. The medicinal creams were topically applied by the patient in an amount (usually about 0.1 cubic centimeter) sufficient to cover the treatment site. Applications were made three times daily and without occlusive dressings. Application periods did not exceed three weeks, and applications were discontinued at any time when resolution of the lesion in the treatment area was clinically judged to be complete. Clinical evaluations of degrees of improvement were made at intervals of daily to weekly.

It was discovered that alphahydroxy acids such as lactic acid, glycolic acid and mandelic acid at a concentration of 2-to-5% in anhydrous bases of the present invention were markedly effective in the treatment of the four patients with severe dry skin.

Complete resolution of the test sites treated with these medicinal compositions was obtained within two-to-three week periods.

(B) Common Dry Skin

Human subjects with mild to moderate degrees of dry skin conditions, as evidenced by dryness, cracking or flaking of the skin, were instructed to apply topically alphahydroxy acids such as atrolactic acid, mandelic acid and lactic acid at concentrations of from 0.2% to 2% in anhydrous bases of the present invention formulated according to the Examples. Twice daily topical application on the affected skin areas was continued for a few weeks. In all the twelve human subjects tested the feeling of skin dryness disappeared after three-to-four days of topical treatment. In all the human subjects treated the rough and cracked skin usually became less pronounced within a week. Generally, the skin appeared normal and felt smooth after about two weeks of topical treatment.

In contrast to the severe dry skin disease the common dry skin condition once restored to normal appearing skin remained improved for some time until causes of dry skin, such as low humidity, cold weather, detergents, soaps, chemicals, etc., recurred. On continued use it was found that twice daily topical application of a composition of the present invention prevented the development of new dry skin lesions.

SUNSCREEN AGENTS

Sunscreen agents such as p-aminobenzoic acid ethyl ester have been incorporated into anhydrous bases of the present invention at a concentration of 5% according to the Example. Human subjects who were prone to sunburn were instructed to topically apply the compositions of the present invention before going out into midday summer sunlight.

It was discovered that p-aminobenzoic acid ethyl ester 5% in anhydrous bases of the present invention was effective in preventing the erythema formation from the sunlight.

The invention may be embodied in other specific forms without departing from the spirit or essential characteristics thereof. The present embodiment is, therefore, to be considered in all respects as illustrative and not restrictive, the scope of the invention being supplemented by the appended claims and all changes which come within the meaning and range of equivalency of the claims are, therefore, intended to be embraced therein.

What is claimed is:

1. An anhydrous non-sticky vehicle for topical application to the human body which vehicle is stable when stored for at least one month at 40° C. and stable when frozen and subsequently thawed at room temperature comprising, in admixture, glyceryl monostearate present in a concentration of from 10–30 percent by weight and a member selected from the group consisting of isopropyl myristate and isopropyl palmitate present in a concentration 30–90 percent by weight of the total composition.

2. The vehicle of claim 1 wherein glyceryl monostearate is present in a concentration of 15–25 percent.

3. The vehicle of claim 1 wherein said member is present in a concentration of 50–80 percent.

4. The vehicle of claim 1 further comprising an occlusive agent selected from the group consisting of mineral oil and petrolatum present in a concentration of less than 30 percent by weight.

5. The vehicle of claim 4 wherein said agent is petrolatum present in a concentration of less than about 20 percent by weight.

6. The vehicle of claim 1 further comprising at least one cosmetic agent selected from the group consisting of sorbitan sesquioleate, sorbitan monooleate, squalene, squalane, beeswax, spermaceti, glyceryl monooleate, beef fat, chicken oil, olive oil, safflower oil and cottonseed oil present in a concentration of no more than about 30 percent by weight.

7. An antiinflammatory medicinal composition for topical application comprising: an antiinflammatory effective amount of a member selected from the group consisting of 6-aminonicotinamide and 6-amionicotinic acid methyl ester; admixed in an anhydrous non-sticky vehicle which is stable when stored for at least one month at 40° C. and stable when frozen and subsequently thawed at room temperature comprising 10–30 percent glyceryl monostearate and 30–90 percent of a member selected from the group consisting of isopropyl myristate and isopropyl palmitate.

8. The composition of claim 7 wherein said vehicle further comprises less than about 30 percent of an occlusive agent selected from the group consisting of mineral oil and petrolatum.

9. An antiinflammatory composition for topical application to involved areas of the human body comprising an antiinflammatory effective amount of dithranol in an anhydrous non-sticky vehicle which is stable when stored for at least one month at 40° C. and stable when frozen and subsequently thawed at room temperature comprising from 10–30 percent glyceryl monostearate and from 30–90 percent of a member selected from the group consisting of isopropyl myristate and isopropyl palmitate.

10. The composition of claim 9 wherein dithranol is present in a concentration of from 0.01 to 0.5 percent.

11. The composition of claim 9 wherein said vehicle comprises less than about 30 percent of an occlusive agent selected from the group consisting of mineral oil and petrolatum.

* * * * *